(12) United States Patent
Prabhu et al.

(10) Patent No.: US 11,771,801 B2
(45) Date of Patent: Oct. 3, 2023

(54) POLYMER SLEEVE FOR INHIBITING STEM WEAR AND IMPROVING TAPER-LOCK IN MODULAR AND NON-MODULAR ORTHOPEDIC IMPLANTS AND THE FABRICATION AND PROCESSING THEREOF

(71) Applicant: Evonik Operations GmbH, Essen (DE)

(72) Inventors: Balaji Prabhu, Hoover, AL (US); Andrew Wood, Birmingham, AL (US); Mahrokh Dadsetan, Birmingham, AL (US); Andreas Karau, Gelnhausen (DE); Harsh Patel, Hoover, AL (US); Marc Knebel, Heddesheim (DE); Suneel Bandi, West Lafayette, IN (US)

(73) Assignee: Evonik Operations GmbH, Essen (DE)

( * ) Notice: Subject to any disclaimer, the term of this patent is extended or adjusted under 35 U.S.C. 154(b) by 872 days.

(21) Appl. No.: 16/617,726

(22) PCT Filed: Jun. 14, 2018

(86) PCT No.: PCT/EP2018/065818
§ 371 (c)(1),
(2) Date: Nov. 27, 2019

(87) PCT Pub. No.: WO2018/229196
PCT Pub. Date: Dec. 20, 2018

(65) Prior Publication Data
US 2020/0108174 A1    Apr. 9, 2020

Related U.S. Application Data

(60) Provisional application No. 62/519,393, filed on Jun. 14, 2017.

(51) Int. Cl.
*A61L 27/26* (2006.01)
*C08L 23/06* (2006.01)
(Continued)

(52) U.S. Cl.
CPC ............... *A61L 27/26* (2013.01); *A61L 27/16* (2013.01); *A61L 27/18* (2013.01); *A61L 27/34* (2013.01);
(Continued)

(58) Field of Classification Search
CPC combination set(s) only.
See application file for complete search history.

(56) References Cited

U.S. PATENT DOCUMENTS 4,840,632 A * 6/1989 Kampner ............ A61F 2/30749
623/22.36
5,037,928 A * 8/1991 Li ...................... A61F 2/30965
425/405.2
(Continued)

FOREIGN PATENT DOCUMENTS

CN    105030377 A  *  11/2015
CN    105030377 A     11/2015
(Continued)

OTHER PUBLICATIONS

International Search Report dated Nov. 16, 2018 in PCT/EP2018/065818 (6 pages).
(Continued)

*Primary Examiner* — Peter A Salamon
(74) *Attorney, Agent, or Firm* — Grüneberg and Myers PLLC

(57) ABSTRACT

The present invention comprises a polymer and/or polymer composite based sleeve to be fitted between an extended body, such the neck, trunnion, and/or stem of a hip implant, and a receiving body, such as a femoral head in a hip
(Continued)

Figure 1:
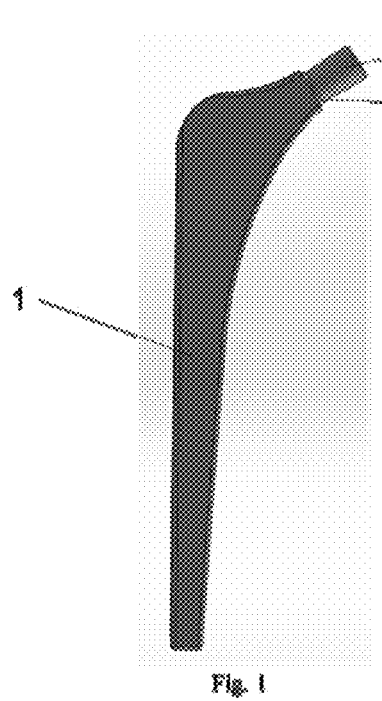

implant, that reduces wear, decreases toxic material from wear debris, enhances the mechanical connection of the extension and receiving body, reduces or eliminates impingement with receiving body, delocalize stress concentrations, and may also serve as a modifying junction between an extension and receiving body of unmatched size. The polymeric based sleeve presently disclosed comprises an inert and/or biologically favorable material which may be used in its virgin form or contain biocompatible additives. In order to best match patient and implant requirements, modifications may be made in the length, thickness, composition, as well as the presence of a taper, or lack thereof, in order to be compatible with existing devices.

15 Claims, 2 Drawing Sheets

(51) Int. Cl.
    *C08L 71/12*     (2006.01)
    *A61L 27/16*     (2006.01)
    *A61L 27/18*     (2006.01)
    *A61L 27/34*     (2006.01)

(52) U.S. Cl.
    CPC ............... *C08L 23/06* (2013.01); *C08L 71/12* (2013.01); *C08L 2203/02* (2013.01); *C08L 2205/025* (2013.01); *C08L 2205/035* (2013.01)

(56) References Cited

U.S. PATENT DOCUMENTS

| | | | |
|---|---|---|---|
| 5,571,193 A * | 11/1996 | Kampner | A61F 2/32 623/23.57 |
| 2005/0267586 A1 * | 12/2005 | Sidebotham | C22C 14/00 623/22.41 |
| 2014/0222158 A1 * | 8/2014 | Lawrynowicz | A61F 2/30767 623/23.12 |
| 2015/0368375 A1 * | 12/2015 | Rodgers, III | C08F 8/00 524/110 |
| 2016/0158016 A1 * | 6/2016 | Jones | A61F 2/30767 623/18.11 |
| 2020/0197562 A1 | 6/2020 | Xue et al. | |

FOREIGN PATENT DOCUMENTS

| | | |
|---|---|---|
| EP | 2 764 849 A1 | 8/2014 |
| JP | H07506739 | 7/1995 |
| JP | 2017000291 A | 1/2017 |

OTHER PUBLICATIONS

Written Opinion dated Nov. 16, 2018 in PCT/EP2018/065818 (11 pages).
Bonfield, "Hydroxyapatite-Reinforced Polyethylene as an Analogous Material for Bone Replacement," copyright Jun. 1988, Annals of the New York Academy of Sciences, vol. 523, No. 1, pp. 173-177.
Dutta et al., "Ceramic and non-ceramic hydroxyapatite as a bone graft material: a brief review," copyright Nov. 2014, Irish Journal of Medical Science, Cahill, Dublin, IE, vol. 184, No. 1, pp. 101-106.

* cited by examiner

POLYMER SLEEVE FOR INHIBITING STEM WEAR AND IMPROVING TAPER-LOCK IN MODULAR AND NON-MODULAR ORTHOPEDIC IMPLANTS AND THE FABRICATION AND PROCESSING THEREOF

CROSS REFERENCE TO RELATED APPLICATIONS

This application is a 35 U.S.C. § 371 U.S. national phase entry of International Application No. PCT/EP2018/065818 having an international filing date of Jun. 14, 2018, which claims the benefit of U.S. Application No. 62/519,393 filed Jun. 14, 2017, each of which is incorporated herein by reference in its entirety.

FIELD OF THE INVENTION

The present disclosure relates to a sleeve for use in orthopedic implant applications that aims to reduce fretting corrosion and subsequent release of metal debris, increase the mechanical connection between the extended body and the receiving body, and/or initiate improved biological response in orthopedic implant devices.

BACKGROUND

With an increasing aging demographic, more active citizens, and a growing number of the population experiencing biological deficiencies, the need for artificial implants has seen rapid growth in the field of public health. A large portion of focus in this area has looked to develop or modify new or existing technologies, respectively, to supply improved materials and methods for large joint replacement/ remediation. The large joints include those belonging to shoulder, hip, knee, and ankle with unique systems having been designed for each in an effort to provide beneficial devices to replace damaged/diseased/dysfunctional native structures.

While metallic based implants offer elevated mechanical properties necessary for large joint implants, they also carry with them deficiencies that decrease their effectiveness, service life, and also introduce possible adverse biological reactions during activities carried out in a patient's everyday life (e.g., walking, squatting, etc.). For example, in total hip replacement, there exists modular implants that allow rapid modifications between components depending on a patient's specific requirements as determined by the surgeon at the time of the procedure. These types of implants contain a number of connections which comprise hard-hard interfaces (metal-on-metal, metal-on-ceramic, etc.) in areas such as taper junctions between the femoral head and its neck, between the stem and neck, and the upper (proximal) and lower (distal) portions of the stem. Each of these interfaces experience micromotions throughout normal patient activities post-procedure and therefore presents a potential site for fretting (i.e., interfacial) wear and subsequent corrosion.

While the metallic materials typically used in these applications (i.e., titanium alloys, cobalt-chromium alloys, surgical grade stainless steel, etc.) are commonly used due to their mechanical robustness and general lack of reaction in biological systems, they pose potential threats as long term implants. These metallic implants exist with a thin oxide surface layer that prevents environmental reaction under most circumstances. However, in large joint implant applications, the micro-motions acting in the joint system throughout daily activities cause removal of sections of the oxide layer thus allowing the metallic substrate to undergo oxidation from surrounding biological fluids. While this oxide layer is able to be re-established on the metallic substrate rather quickly, the reactions occurring in its absence may induce the release of heavy metal ions, generate hydrogen atoms (therefore producing an acidic environment), and lead to oxidation of the metallic component. Subsequently, cyclic loading of these implants repeats this process and can ultimately lead to revisionary procedures due to mechanical property degradation of the implant, osteolysis, and/or pseudotumor formation. Further, a common complaint among patients who have received, for example, a total hip replacement procedure, commonly complain of pain during daily activities due to the grinding of the hard-on-hard surfaces.

Another common complaint among patients receiving large joint implants is that of a limited range of motion. For example, in patients who have received total hip arthroplasty, impingement of the femoral neck into the acetabulum is a common complaint if the implant was not fitted properly upon implantation. This issue is a common cause for revisionary procedures for the fact that either the patient's range of motion is drastically limited or, in more consequential cases, the impingement of the femoral neck into the acetabulum has caused mechanical damage to the implant. These revisionary procedures typically require the patient to receive a larger diameter femoral head which allows for a larger impingement-free range of motion. To accommodate this larger diameter femoral head, a modifying sleeve may be used, such as the present invention put forth herein, to accommodate the change in diameter size of the implant neck and the newly implanted femoral head receiving bore.

Recent work has been conducted on metallic implants and identifying potential replacement materials for them due to a variety of deficiencies they carry. While metallic implants offer low cost production of a device with high mechanical properties and typical bio-inertness, the drawbacks they have call for development of a better solution. Stress-shielding, radiopacity, and presence of heavy metal ions from fretting wear and corrosion are among the concerns being addressed by current research.

Stress-shielding has become a topic of increasing interest in large joint implants. The use of the typical metallic materials is largely to blame for this effect since their mechanical properties are much higher than that typically found in native bone systems. Problems arising from this stress-shielding phenomena are that the one being shielded from stress may have a loss of bone stock where the bone is resorbed (osteolysis) which can lead to aspectic loosening of the joint and subsequent failure of the implant or even fracture of the bone. The adoption of a material which has bone-like mechanical properties serving as an interface between two different materials (implanted or native) can serve to distribute the stresses and strains upon loading therefore mimicking natural bone response.

The latter deficiency, the presence of heavy metal ions, is typically encountered in implantable devices and is a side-effect of the wear induced particle production caused by normal patient activities. Upon being scratched, these metallic substrates release heavy metal ions, such as chromium and/or molybdenum, among other, into the patient's bloodstream and can cause negative effects. More so, even if these heavy metal ions are not present in a patient, many citizens have allergic responses to metallic materials typically used in this area thus furthering the point that a solution needs to be found for this problem.

A culmination of these two issues, although these are not the only issues with the current designs, is found, for example, in taper mismatch. Both modular and non-modular hip implants have a tapered neck which rests in the femoral head after implantation. Even when the same manufacturer produces both the neck and the femoral head, without a perfect assembly during the surgical procedure, one circumference of the implant neck (either the proximal or distal end of the neck residing inside the femoral head) is the only one in contact with the interior diameter of the femoral head. If the taper alignment was perfect, the stresses and strains placed on the implant during normal activities would be evenly distributed across the neck and femoral head interior. However, perfect alignment is never achieved and these points of contact between the proximal or distal end of the neck and the interior bore of the femoral head serve as stress concentration points which can lead to increased wear (fretting corrosion), and/or crack initiation, propagation, and growth leading to a catastrophic failure of the implant. By introducing a sleeve such as the invention presented herein, even with a taper alignment mismatch, the sleeve interface is able to dissipate and distribute the stresses and strains on the implant allowing for a reduction in risk of fretting corrosion and catastrophic failure.

Recently, metallic based sleeves (typically titanium) have been produced in an effort to offer even greater modification ability during procedure where various components must be fitted together. With this type of device, the up-sizing of, for instance, the stem to better fit a larger femoral head, can achieve better fit but the sleeves still have an unmatched taper angle with the femoral head. In this present example, mechanical loads and motions are therefore only imparted at the location of contact between the femoral head, sleeve, and trunnion causing high stress concentrations in these areas. Further, the use of such devices offers no increase in mechanical resistance to catastrophic failure as these hard materials (metallic, ceramic, or their combinations) are unable to dissipate energy and can lead to failure.

With the onset of using ceramic-on-metal and/or polymer-on-metal joint systems, the rate of wear on the metallic materials was subdued, but not entirely removed. While these ceramic-on-metal components typically offer improved wear properties, the presence of fretting corrosion, defined as corrosion at the contact surfaces of two rough materials, still remains. Further, the possibility of catastrophic failure of the brittle ceramic material during high impact loads and/or chipping of the material represent a small but significant deficiency of current systems.

This introduction of hard-on-soft implants has seen rapid growth in recent years due to the recent findings of better wear resistance, a lessened chance of catastrophic failure, and increased patient comfort when a hard surface was articulating against a soft polymeric surface. Predominantly, a form of polyethylene is chosen to serve as the polymeric surface in these applications. Although its use is common, recent studies have shown that this polymeric material may be less than ideal for such applications. For instance, ultra-high molecular weight polyethylene (UHMWPE) is used in a majority of knee and hip implants as the tibial component or the acetabular liner, respectively, due to wear rates and improved patient comfort. However, the oxidation of this material in vivo leads to degradation of the implant and loss of mechanical properties resulting in failure of the component. In an effort to remedy this problem, a crosslinked UHMWPE (X-UHMWPE) was developed. While this helped to alleviate the in vivo oxidation of the implant, the crosslinking procedure typically decrease the mechanical properties, such as ductility and fracture toughness, of the implant which is undesirable. Recent studies have shown that a new polymeric material may be more beneficial than trying to repair the deficiencies found in the current polyethylene based materials.

Despite recent advances, the industry still lacks polymeric orthopedic implantable components directed to hard-on-hard surfaces (metal-on-metal, ceramic-on-metal, etc.) and interfaces between implant material and native biological structures. Such interfaces are typical locations for fretting corrosion, implant impingement, stress concentration, and/or mechanical failure stemming from implant deficiencies such as differing materials, taper misalignment, frictional micro-motions, and/or patient specific reactions. The present invention aims to reduce these undesirable results by acting as a boundary at the interface of these surfaces so as to reduce the frictional wear, decrease the intensity of stress concentrations zones, act as a spacer to decrease chance of impingement, and act as a system to prompt desirable biological response for an intended application

SUMMARY

The present invention comprises of a polymeric spacer device generally consisting of a high-strength, high-elongation material with appropriate stiffness so as to avoid the introduction of stress-shielding to the implant. Application of the herein disclosed device to the implant stem may be accomplished by mechanical means or during fabrication of the implant. Once in place, the disclosed device is multi-functional in that it may:
  (i) Reduce the amount of wear between the extended body and the receiving body therefore reducing the probability of fretting corrosion and subsequent release of heavy metal ions and/or mechanical failure.
  (ii) Enhance the mechanical adherence between the stem the extended body and the receiving body therefore reducing the likelihood of implant separation.
  (iii) Act as an interface between two components serving to reduce stress concentration zones and the subsequent the risk of catastrophic failure.
  (iv) Serve as a modifying junction between a stem of one exterior size the extended body and the receiving body of a separate interior dimension.

In one embodiment of the present invention, the device may be placed between the trunnion sleeve of a hip implant stem and the inner diameter of the femoral head to reduce wear, increase mechanical rigidity, and fit custom sized implants.

DRAWINGS

Some embodiments of the present invention are illustrated as an example and are not limited by the figures of the accompanying drawing, in which like references may indicate similar elements and in which:

FIG. 1 depicts an overview of a typical hip implant with each main section of the implant, stem 1, trunnion 2, and neck 3, indicated.

Figure 2:
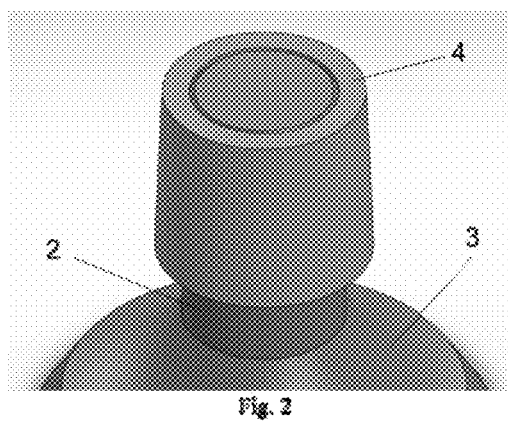

FIG. 2 illustrates an enhanced view of the present invention in a fully-bored configuration 4 fitted onto the implant trunnion 2 at the end of the implant neck 3.

Figure 3:
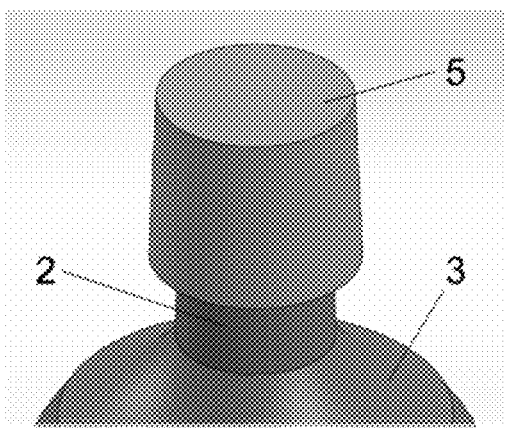

FIG. 3 illustrates an enhanced view of the present invention in a partially-bored configuration 5 fitted onto the implant trunnion 2 at the end of the implant neck 3.

Figure 4:
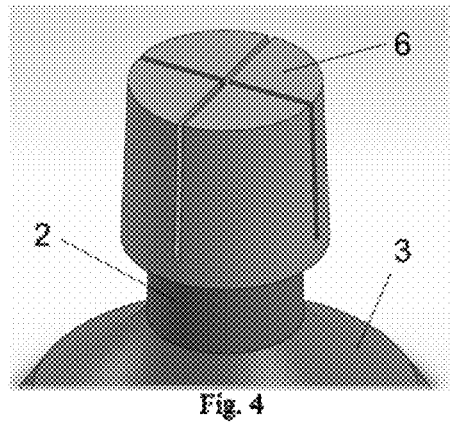

FIG. 4 illustrates an enhanced view of the present invention in an adaptable-taper configuration 6 fitted onto the implant trunnion 2 at the end of the implant neck 3.

Figure 5:
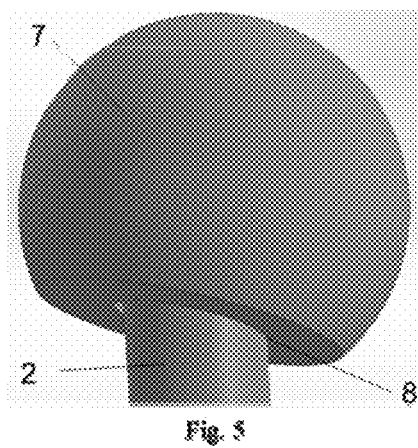

FIG. 5 illustrates an enhanced view of the typical femoral head implant 7 fitted onto the hip implant trunnion 2 without the present invention in place which can lead to impingement 8 between the trunnion 2 and femoral head 7.

Figure 6:
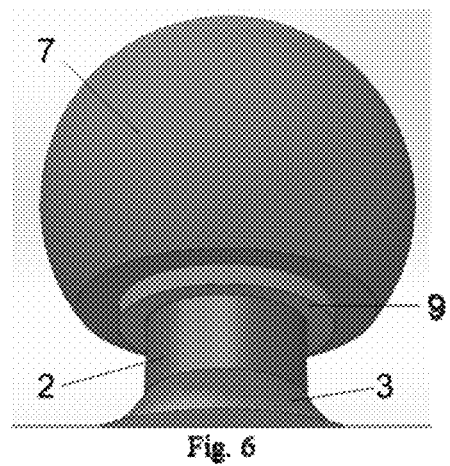

FIG. 6 illustrates an enhanced view of the typical femoral head implant 7 fitted onto the hip implant trunnion 2 with the present invention 9 with design consistent with 9, in place which can lower the risk of impingement between the trunnion 2, neck 3, and femoral head 7.

Figure 7:
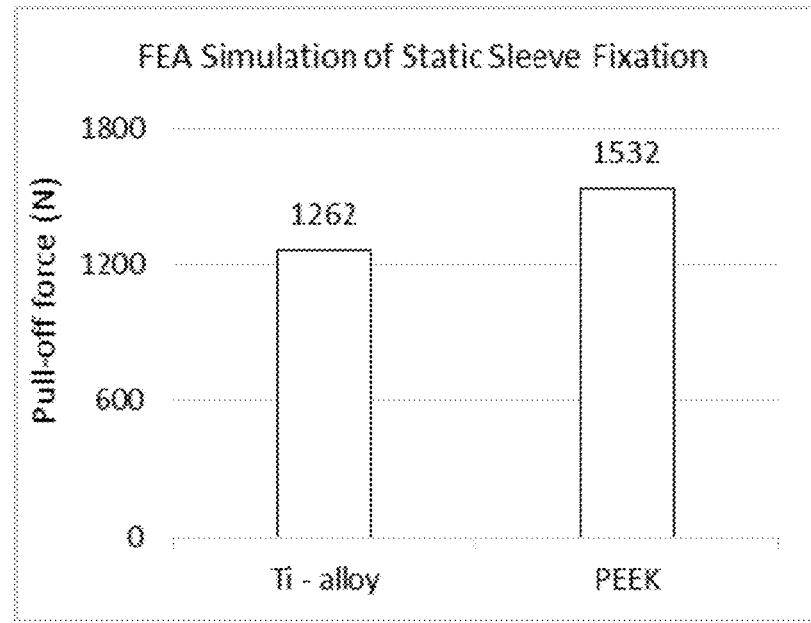

FIG. 7 illustrates a finite elemental analysis of PEEK Sleeves fixation strength in a hip implant gives an indication of the stability of the femoral head to the hip stem in the implant.

Figure 8:
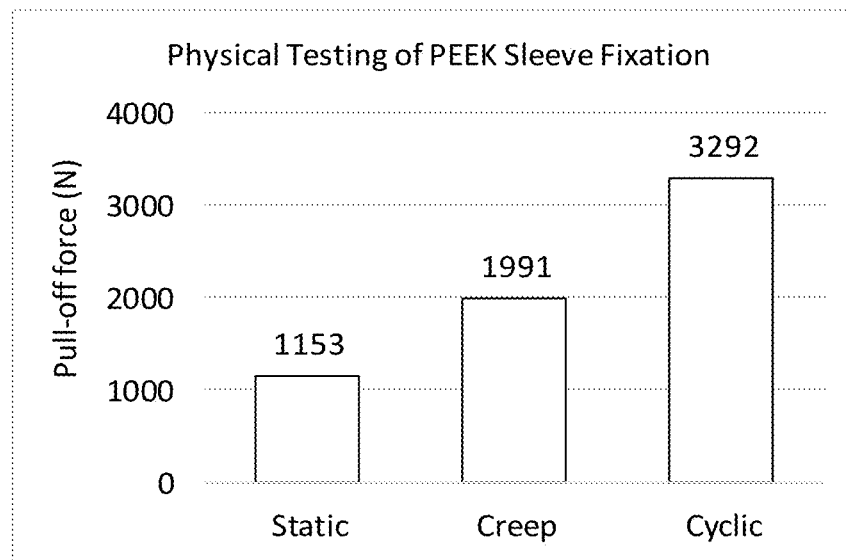

FIG. 8 illustrates a physical testing of PEEK Sleeves fitted between a femoral hip stem and a femoral head indicate pull-off forces over 1 kN for all tested scenarios. The increase for pull-off force with creep and even further with cyclic indicates that the stability of the implant increases with use of the PEEK Sleeve as the femoral head is able to seat further and more effectively to the femoral hip stem.

DETAILED DESCRIPTION OF THE INVENTION

The terminology used herein is chosen for the purpose of describing particular embodiments of the invention but are not intended to impart limitations of the invention. Herein, the term "and/or" includes any and all combinations of one or more of the associated listed items. Further, the terms "comprises" and/or "comprising" is to be understood in the specification to specify the presence of stated features, procedures, components, elements, geometries, and/or other characteristics, but do not impede the presence and/or addition of one or more further features, procedures, components, elements, geometries, and/or other characteristics thereof.

Unless otherwise defined, all terms, including those scientific and/or technical in nature, are to be understood to have the same meanings as those commonly understood by one having ordinary skill in the art of the invention. Further, terms such as those of a common nature, should be interpreted as having a meaning that is consistent with their meaning in the scope of the relevant art and/or the present disclosure and shall not be interpreted in an overly formal sense without the term being expressly defined so herein.

In describing the herein disclosed invention, it will be understood that a number of techniques and/or steps are disclosed. Each of these stated techniques and/or steps has individual benefit and each can also be used in conjunction with one or more of the other herein disclosed techniques and/or steps. Therefore, this description will refrain from repeating all possible combinations of these individual steps in an unnecessary fashion for the sake of clarity but is not to be understood as limiting the possible techniques and/or steps that lie within the scope of the invention and claims.

A new component, preferred (but not limiting) embodiments, composite specifications, and methods for positioning the present invention are discussed herein. In the following description, for purposes of explanation, specific details are set forth in order to provide a thorough understanding of the present invention. It will be evident, however, to one skilled in the art that the present invention may be practiced without these specific details.

The disclosure herein is to be considered only as an exemplification of the invention and is not to be understood as a limitation of the invention to the specific embodiments which are illustrated by the descriptions and figures herein.

The present invention will now be described by referencing the appended figures representing preferred embodiments, but not limiting potential embodiments of the present invention. FIG. 1 depicts a typical hip implant showing the hip stem 1, trunnion 2, and neck 3.

A close-up perspective view of a preferred embodiment of the present invention is shown in FIG. 2 but does not limit potential embodiments of the present invention. A tapered or non-tapered, fully-bored sleeve 4 is placed onto a tapered or non-tapered trunnion 2 at the proximal end of the neck 3. This trunnion 2 may exist on a neck 3 as a component of a single assembly of the implant as a whole or as part of a modular component comprising of its own trunnion 2 and neck 3 that is able to be attached to a different implant. The attachment of the tapered or non-tapered, fully-bored sleeve 4 to the trunnion 2 may be carried out via mechanical forces (i.e., pushing, pulling, stretching, etc.) to place the fully-bored, tapered or non-tapered sleeve 4 onto the trunnion 2 or through thermal methods where the fully-bored, tapered or non-tapered sleeve 4 is thermally formed around the external tapered or non-tapered diameter of the trunnion 2.

A close-up perspective view of a preferred embodiment of the present invention is shown in FIG. 3 but does not limit potential embodiments of the present invention. The partially-bored, tapered or non-tapered sleeve 5 would be fitted onto the trunnion 2 at the proximal end of the neck 3. This trunnion 2 may exist on a neck 3 as a component of a single assembly of the implant as a whole or as part of a modular component comprising of its own trunnion 2 and neck 3 that is able to be attached to a different implant. This attachment of the partially-bored, tapered or non-tapered sleeve 5 to the trunnion 2 may be carried out via mechanical forces (i.e., pushing, pulling, stretching, etc.) on the partially-bored, tapered or non-tapered sleeve 5 onto the trunnion 2 or through thermal methods where the partially-bored, tapered or non-tapered sleeve 5 is thermally formed around the external diameter of the trunnion 2.

A close-up perspective view of a preferred embodiment of the present invention is shown in FIG. 4 but does not limit potential embodiments of the present invention. The partially-bored, angle-adaptable, tapered or non-tapered sleeve 6 containing gaps along the longitudinal surface of the sleeve to allow for angle modification would be fitted onto the trunnion 2 at the proximal end of the neck 3. This trunnion 2 may exist on a neck 3 as a component of a single assembly of the implant as a whole or as part of a modular component comprising of its own trunnion 2 and neck 3 that is able to be attached to a different implant. This attachment of the partially-bored, angle-adaptable, tapered or non-tapered sleeve 6 to the trunnion 2 may be carried out via mechanical forces (i.e., pushing, pulling, stretching, etc.) on the partially-bored, angle-adjustable, tapered or non-tapered sleeve 6 onto the trunnion 2 or through thermal methods where the partially-bored, angle-adaptable, tapered or non-tapered sleeve 6 is thermally formed around the external diameter of the trunnion 2.

A close-up perspective view of a preferred embodiment of the present invention is shown in FIG. 5 but does not limit potential embodiments of the present invention. In this particular example, but not limitation of the present invention, the sleeve 9 is not present between the femoral head 7 and the trunnion 2. This leads to impingement 8 of the femoral head 7 onto the trunnion 2 and can lead to advanced wear and/or catastrophic failure or chipping of the femoral head 7 depending on the type of material chosen.

A close-up perspective view of a preferred embodiment of the present invention is shown in FIG. 6 but does not limit potential embodiments of the present invention. In this particular example, but not limitation of the present invention, the sleeve 9 is present between the femoral head 7 and the trunnion 2. This may reduce the probability of impingement 8 of the femoral head 7 onto the trunnion 2 and can decrease the advanced wear and/or catastrophic failure or chipping of the femoral head 7 that may occur if the sleeve 9 is not in place.

In preferred embodiments, the sleeve 9 is fitted between two opposing surfaces which would otherwise be in direct contact. The sleeve 9 may be comprised of any polymeric based material or polymer-composite where the polymer composite contains wear-resistant particle material and/or elements (metal, ceramic, or polymeric material) and/or biologically favorable composites.

In a more preferred embodiment the sleeve is part of a medical implant.

A further preferred embodiment is that where in the sleeve is fitted around the femoral stem which will reside in the femoral cavity. The sleeve may be fitted onto the femoral stem via mechanical forces (i.e., pushing, pulling, stretching, etc.) or thermal methods where the sleeve is fitted on the femoral stem during thermal processing. In this embodiment, the sleeve may comprise a neat, virgin polymeric material or a composite material for improved biological response. In this example, but not limiting, embodiments, the sleeve may allow for faster and more efficient bone regeneration and response as well as removal of stress-shielding commonly associated with this area of the hip implant.

In a more preferred embodiment the polymeric sleeve is placed onto an extended body, wherein the extended body is a neck, a trunnion, a stem of a hip implant, a stem of the glenosphere, or a humeral component in a shoulder implant, wherein the extended body is placed into a receiving body, wherein the receiving body is a femoral head in a hip implant, a humeral component, or a metaglene in shoulder implants.

More preferably the extended body and receiving body is comprised of a metallic particle, a ceramic particle, a polymeric material, or a mixture thereof.

More preferably the inventive sleeve is of a tapered or non-tapered geometry.

More preferably the inventive sleeve is partially or fully bored with openings at the proximal and distal ends. Still more preferably the sleeve is partially bored with a solid surface remaining at either the proximal or distal end.

More preferably the inventive sleeve has an angle of the taper, wherein the angle of the taper is adjustable between 5 and 7 degrees.

The inventive sleeve has improved wear resistance, improved mechanical properties, improved coefficient of friction, improved taper lock, improved biological response, or improved wear resistance as compared to a non-polymeric sleeve. Furthermore it is less affected by corrosion as compared to a non-polymeric sleeve under static and dynamic conditions.

In a still more preferred embodiment the polymeric sleeve comprises an internal surface and an external surface, wherein the thickness measured from the internal surface to the external surface of the polymeric sleeve is between 0.2 and 20 mm. The polymeric sleeve comprises a distal end and a proximal end, wherein the height measured from the distal end to the proximal end of the sleeve is between 5 and 50 mm.

In preferred embodiments, the polymeric material for the polymeric sleeve includes but is not limited to polyaryletherketone (PAEK polymers, including but not limited to PEEK, PEKK, PEKEKK, and other polymerization material of the parent material of PAEKs consisting of a backbone of alternating ether and ketone bonds contacting, or not containing, crosslinked polymer chains), polyetheretherketone (PEEK, poly-ether-ether-ketone, and other embodiments of the parent polymer, PAEKs, containing, or not containing, crosslinked polymeric chains), polyethylene (PE, UHMWPE, crosslinked PE, Vitamin-E infused PE, and other embodiments and compounds of the parent polymer), and/or other biologically favorable and mechanically robust polymeric material. Further preferred materials are polyaryletherketones including PEEK, PEKK, PEKEKK with its common meanings. Still more preferably the polyaryletherketone material is a high density material with a minimum of porosity.

In preferred embodiments, the polymeric composite material for the polymeric sleeve comprises a polymeric material and a reinforcing particle. The polymeric material includes but is not limited to polyaryletherketone (PAEK polymers, including but not limited to PEEK, PEKK, PEKEKK, and other polymerization material of the parent material of PAEKs consisting of a backbone of alternating ether and ketone bonds contacting, or not containing, crosslinked polymer chains), polyetheretherketone (PEEK, poly-ether-ether-ketone, and other embodiments of the parent polymer, PAEKs, containing, or not containing, crosslinked polymeric chains), polyethylene (PE, UHMWPE, crosslinked PE, Vitamin-E infused PE, and other embodiments and compounds of the parent polymer), and other biologically favorable and mechanically robust polymeric material. The reinforcing particle includes but is not limited to carbon particles (both pitch-based and PAN-based), glass particles, metal particles, ceramic particles, or a mixture thereof.

The inventive sleeve may be fabricated with any method of the art, preferably through blending, compounding, extruding, compression molding, injection molding, hot pressing, hot isostatic pressing, or a combination thereof. More preferably the sleeve is manufactured in a two step process, where the first step is a thermal process like extrusion or compression molding and the second step is a mechanical form giving process. Particularly preferred sleeve is manufactured in the first step by extrusion and in the second step by cutting like CNC machine finishing.

Preferably the sleeve is a medical implant made out of polyaryletherketon, including PEEK, PEKK, PEKEKK. Preferably the implant is a joint implant, more preferably the joint implant consist of two parts e.g. an extended body is placed into a receiving body, where the extended body and receiving body is comprised of a metallic particle, a ceramic particle, a polymeric material, or a mixture thereof.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Finite Element Analysis:

Static Loading

A 3,000 N axial load was used to assemble a 32 mm diameter ceramic head, a PEEK sleeve made of VESTA-KEEP® of the I-grade (Trademark of Evonik, Germany), and a 12/14 titanium-alloy stem. Subsequently, the load was ramped to 8,700 N to simulate peak loading during stair climbing (Bergmann, G., Graichen, F. & Rohlmann, A. Hip joint loading during walking and running, measured in two patients. J. Biomech. 26, 969-990 (1993)). The axial force was then reversed and the force needed to displace the assembly of the ceramic head from the 12/14 titanium-alloy stem was calculated and reported as "Pull-off Force".

The importance of the test is that the static loading is a direct comparison of the initial stability the implant system has after assembly by the surgeon. The force measured in this test can be seen as the amount of force required for a surgeon to remove the ceramic head from the hip stem directly after implantation of the system with a PEEK sleeve. This translates to the immediate stability felt by the patient after surgery where a higher pull-off force should translate to a more stable feeling joint implant.

Creep Test

A 3,000 N axial load was used to assemble a 32 mm diameter ceramic head, a PEEK sleeve made of VESTA-KEEP® of the I-grade, and a 12/14 titanium-alloy stem. After this assembly force was applied, the force was ramped down to 0 N and kept at 0 N for 1,000 minutes as done in previous studies (Dropik, M. J., Johnson, D. H. & Roth, D. E. Developing an ANSYS Creep Model for Polypropylene from Experimental Data. Conf. Proc. International ANSYS Conference 161, (2002)). After this holding time of 1,000 minutes, the pull-off force was tested in a similar manner to that for the Static Loading condition.

Physical Testing:

Static Loading

A 3,000 N axial load was used to assemble a 32 mm diameter ceramic head, a PEEK sleeve made of VESTA-KEEP® of the I-grade, and a 12/14 titanium-alloy stem. Subsequently, the load was ramped to 8,700 N to simulate peak loading during stair climbing (Bergmann, G., Graichen, F. & Rohlmann, A. Hip joint loading during walking and running, measured in two patients. J. Biomech. 26, 969-990 (1993)). The axial force was then reversed and the force needed to displace the assembly of the ceramic head from the 12/14 titanium-alloy stem was calculated and reported as "Pull-off Force".

The importance of this test is that the static loading is a direct comparison of the initial stability the implant system has after assembly by the surgeon. The force measured in this test can be seen as the amount of force required for a surgeon to remove the ceramic head from the hip stem directly after implantation of the system with a PEEK sleeve. This translates to the immediate stability felt by the patient after surgery where a higher pull-off force should translate to a more stable feeling joint implant.

Cyclic Loading

A 12/14 titanium-alloy stem and PEEK sleeve made of VESTAKEEP® of the I-grade were mated with a stainless steel model of a femoral head with all geometries matching that of the 32 mm ceramic head used in the finite element analysis model. The 3,000 N assembly force was applied at a loading rate of 500 N/s in accordance with ISO 7206-10. Following initial assembly, cyclic axial loading between 100 N and 5,000 N was applied to the stem/sleeve/block assembly for 1.2 million cycles at 1 Hz. At the end of the cyclic test, a stem pull-off test was performed at a stroke rate of 0.008 mm/s following ISO 7206-10. Application of 3,000 N caused the assembly to displace 0.90 mm in the axial direction. Ramping the load to 5,000 N caused to assembly to displace an additionally 0.43 mm giving the total displacement from 0 N to 5,000 N of 1.33 mm. While cycling the load between 100 N and 5,000 N, displacement was measured to be 0.09 mm. Upon completion of 1.2 million cycles, the pull-off force was measured to be 3,292 N.

Creep Test

In the second physical test, a 12/14 titanium-alloy stem and extra-large sleeve made of VESTAKEEP® of the I-grade were mated with a machined stainless-steel block by application of a 3,000 N axial load per ISO 7206-10. The load was then ramped down to 0 N and maintained at zero load for 1,000 minutes after which pull-off forces were measured. The head displaced 0.86 mm relative to the stem when loading from 0 N to 3,000 N. After unloading to 0 N and holding at no load for 1,000 minutes, the pull-off force was measured to be 1,991 N. Pull-off forces achieved with PEEK sleeves are comparable to values reported by others investigating pull-off forces of titanium stems and ceramic heads. (Rehmer, A., Bishop, N. E. & Morlock, M. M. Influence of assembly procedure and material combination on the strength of the taper connection at the head-neck junction of modular hip endoprostheses. Clin. Biomech. Bristol Avon 27, 77-83 (2012)) measured pull-off forces ranging between 1,500 N to 2,000 N after applying a 3,000 N assembly force. Similarly, (Faizan, A., Longaray, J. & Lee, R. Does trunnion cleaning method affect the taper interface? Conf. Proc. Orthopaedic Research Society (ORS), San Diego, (2017)) reported an average 1,000 N pull-off force for titanium stems and ceramic heads assembled with 2,000 N.

What is claimed is:

1. A polymeric sleeve for an implant, the polymeric sleeve comprising a polymeric material wherein the polymeric sleeve comprises a distal end and a proximal end, wherein the height measured from the distal end to the proximal end of the sleeve is between 5 and 50 mm, and wherein the polymeric sleeve has an angle of the taper, wherein the angle of the taper is adjustable between 5 and 7 degrees.

2. The polymeric sleeve of claim 1, wherein the polymeric material is selected from the group consisting of polyaryletherketone, polyetheretherketone, and polyethylene, and wherein the implant is a joint implant including an extended body and a receiving body.

3. The polymeric sleeve of claim 2, wherein the polyaryletherketone comprises PEEK, PEKK, PEKEKK, and other polymerization material of the parent material of PAEKs consisting of a backbone of alternating ether and ketone bonds contacting, or not containing, crosslinked polymer chains.

4. The polymeric sleeve of claim 2, wherein the polyetheretherketone comprises PEEK, poly-ether-ether-ketone, and other polymerization material of the parent polymer, PAEKs, containing, or not containing, crosslinked polymeric chains.

5. The polymeric sleeve of claim 2, wherein the polyethylene comprises PE, UHMWPE, crosslinked PE, Vitamin-E infused PE, and other polymerization material and compounds of the parent polymer.

6. The polymeric sleeve of claim 1, wherein the polymeric sleeve is placed onto an extended body, wherein the extended body is a neck, a trunnion, a stem of a hip implant, a stem of the glenosphere, or a humeral component in a shoulder implant, wherein the extended body is placed into a receiving body, wherein the receiving body is a femoral head in a hip implant, a humeral component, or a metaglene in shoulder implants.

7. The polymeric sleeve of claim 6, wherein the extended body and receiving body comprises a metallic particle, a ceramic particle, a polymeric material, or a mixture thereof form prior to manufacture into the extended body or receiving body.

8. The polymeric sleeve of claim 1, wherein the polymeric sleeve comprises an internal surface and an external surface, wherein the thickness measured from the internal surface to the external surface of the polymeric sleeve is between 0.2 and 20 mm.

9. The polymeric sleeve of claim 1 is of a tapered or non-tapered geometry.

10. The polymeric sleeve of claim 1, wherein the polymeric sleeve is fully bored with openings at the proximal and distal ends.

11. The polymeric sleeve of claim 1, wherein the polymeric sleeve is partially bored with a solid surface remaining at either the proximal or distal end.

12. The polymeric sleeve of claim 1, where an additive material comprise up to 50% by weight of the polymeric sleeve.

13. The polymeric sleeve of claim 1 is fabricated through blending, compounding, extruding, compression molding, injection molding, hot pressing, hot isostatic pressing, or a combination thereof.

14. The polymeric sleeve of claim 1 has improved wear resistance, improved mechanical properties, improved coefficient of friction, improved taper lock, improved biological response, or improved wear resistance as compared to a non-polymeric sleeve.

15. The polymeric sleeve of claim 1 is less affected by corrosion as compared to a non-polymeric sleeve under static and dynamic conditions.

* * * * *